(12) United States Patent
Baxter et al.

(10) Patent No.: US 10,670,614 B2
(45) Date of Patent: *Jun. 2, 2020

(54) HEMOLYSIS DETECTION DEVICE, SYSTEM AND METHOD

(71) Applicant: Siemens Healthcare Diagnostics Inc., Tarrytown, NY (US)

(72) Inventors: Andrew John Baxter, Sudbury (GB); Paul William Cotton, Halstead (GB)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/514,304

(22) Filed: Jul. 17, 2019

(65) Prior Publication Data

US 2019/0339293 A1    Nov. 7, 2019

Related U.S. Application Data

(63) Continuation of application No. 15/513,429, filed as application No. PCT/US2015/052926 on Sep. 29, 2015, now Pat. No. 10,386,374.

(Continued)

(51) Int. Cl.
*G01N 33/72* (2006.01)
*G01N 33/49* (2006.01)
(Continued)

(52) U.S. Cl.
CPC ......... *G01N 33/721* (2013.01); *G01N 33/491* (2013.01); *G01N 33/4925* (2013.01); *G01N 33/726* (2013.01); *A61M 1/34* (2013.01); *G01N 33/483* (2013.01); *G01N 33/49* (2013.01); *G01N 33/50* (2013.01); *G01N 33/72* (2013.01);
(Continued)

(58) Field of Classification Search
CPC . A61M 1/34; G01N 2015/055; G01N 33/483; G01N 33/49; G01N 33/491; G01N 33/492; G01N 33/4925; G01N 33/50; G01N 33/72; G01N 33/721; G01N 33/726;
(Continued)

(56) References Cited

U.S. PATENT DOCUMENTS 4,274,978 A    6/1981  Moore
5,593,638 A *  1/1997  Davis ................... G01N 33/725
                                                    422/402

(Continued)

FOREIGN PATENT DOCUMENTS

DE    69432122 T2    10/2003
WO    9510044 A1    4/1995
(Continued)

OTHER PUBLICATIONS

International Search Report and Written Opinion of International Application No. PCT/US2015/052926 dated Dec. 30, 2015.

(Continued)

*Primary Examiner* — Maureen Wallenhorst
(74) *Attorney, Agent, or Firm* — Dunlap Codding P.C.

(57) ABSTRACT

Aspects of the present invention are directed to devices, systems and methods that enable the quick and reliable detection of hemolysis in a sample such that a sample which exhibits an unacceptable level of hemolysis can be flagged or disregarded in an associated diagnostic test.

4 Claims, 2 Drawing Sheets

Related U.S. Application Data

(60) Provisional application No. 62/057,452, filed on Sep. 30, 2014.

(51) Int. Cl.
*G01N 33/483* (2006.01)
*G01N 33/84* (2006.01)
*G01N 33/50* (2006.01)
*G01N 33/80* (2006.01)
*G01N 15/05* (2006.01)
*A61M 1/34* (2006.01)

(52) U.S. Cl.
CPC ............ *G01N 33/80* (2013.01); *G01N 33/84* (2013.01); *G01N 2015/055* (2013.01); *Y10T 436/255* (2015.01)

(58) Field of Classification Search
CPC ...... G01N 33/80; G01N 33/84; Y10T 436/25; Y10T 436/25375; Y10T 436/255; Y10T 436/11
USPC .. 436/43, 63, 66, 68, 74, 79, 164, 165, 171, 436/174, 177, 178; 435/288.7; 422/82.05, 82.09, 527, 535, 554
See application file for complete search history.

(56) References Cited

U.S. PATENT DOCUMENTS

| | | | |
|---|---|---|---|
| 5,902,253 A | 5/1999 | Pfeiffer et al. | |
| 7,125,493 B2 | 10/2006 | Wang et al. | |
| 7,744,820 B2 * | 6/2010 | Togawa | B01D 61/18 210/348 |
| 8,846,333 B2 * | 9/2014 | Karlsson | A61B 5/15003 435/2 |
| 9,045,792 B2 * | 6/2015 | Karlsson | A61B 5/14546 |
| 10,386,374 B2 * | 8/2019 | Baxter | |
| 2002/0122168 A1 | 9/2002 | Garcia-Rubio et al. | |
| 2003/0082076 A1 | 5/2003 | Lin et al. | |
| 2004/0170535 A1 * | 9/2004 | Noda | G01N 33/525 422/535 |
| 2012/0088227 A1 * | 4/2012 | Gruebl | B01L 3/5023 435/5 |
| 2012/0275955 A1 | 11/2012 | Haghgooie et al. | |
| 2012/0277697 A1 | 11/2012 | Haghgooie et al. | |
| 2013/0052675 A1 * | 2/2013 | Karlsson | A61B 5/14546 435/15 |
| 2013/0084592 A1 | 4/2013 | Seiple | |
| 2014/0072996 A1 | 3/2014 | Adamczyk et al. | |
| 2014/0191138 A1 | 7/2014 | Atzler et al. | |

FOREIGN PATENT DOCUMENTS

| | | | |
|---|---|---|---|
| WO | 2011/040874 | * | 4/2011 |
| WO | 2011040874 A1 | | 4/2011 |
| WO | 2012036622 A1 | | 3/2012 |
| WO | 2013/085462 | * | 6/2013 |
| WO | 2013085462 A1 | | 6/2013 |

OTHER PUBLICATIONS

Webb, Sarah, "Low-Cost Device Quickly Isolates Blood Plasma", Oct. 15, 2013, Chemical & Engineering News, pp. 1-3.

Pall Life Sciences, "VividTM Plasma Separation Membrane", Product Data, 2009, pp. 1-6.

Fishkin et al., "Frequency-Domain Method for Measuring Spectral Properties in Multiple-scattering Media: Methemoglobin Absorption Spectrum in a Tissuelike Phantom", Mar. 1, 1995, Applied Optics, vol. 34, No. 7, pp. 1143-1155.

Viera et al., "Measurement of Whole Blood Potassium—Is it Clinically Safe?", 2003, Clinical Chemistry 49 No. 12, pp. 2105-2106.

Han et al., "A Comparative Study of Common Techniques Used to Measure Haemolysis in Stored Red Cell Concentrates", 2009, Vox Sanguinis, pp. 1-8.

Blood and Hemoglobin, Experiment 10, available at <http://courses.chem.indiana.edu/c122/documents/Experiment10_BloodandHemoglobin.pdf>, date retrieved from Internet Archive Wayback Machine—Jun. 30, 2010, pp. 1-16.

Examination Report of European Application No. 15846601.1 dated Apr. 24, 2018.

European Search Report and Written Opinion of European Application No. 158466011 dated Aug. 1, 2017.

* cited by examiner

HEMOLYSIS DETECTION DEVICE, SYSTEM AND METHOD

This application is a continuation of U.S. Ser. No. 15/513,429, filed Mar. 22, 2017, now U.S. Pat. No. 10,386,374, which claims the benefit of U.S. National Stage of International Application No. PCT/US2015/052926, filed Sep. 29, 2015 and claims priority under 35 U.S.C. 119(e) to U.S. Provisional Application No. 62/057,452, filed Sep. 30, 2014. All of the applications are incorporated by reference herein in their entirety.

FIELD OF THE INVENTION

The present invention relates to diagnostic testing, and more particularly to devices, methods, and systems for rapidly scanning samples for hemolysis prior to subjecting the same samples to one or more analytical tests.

BACKGROUND OF THE INVENTION

Point-of-care testing refers generally to medical testing at or near the site of patient care, such as in an emergency room. A desired outcome of such tests is often to obtain rapid and accurate lab results to determine a next course of action in patient care. A number of such point of care tests involve taking or otherwise using a blood sample from a patient. The ideal blood sample is pure plasma separated from the source whole blood sample. Hemolysis (haemolysis), however, is a common problem which may introduce undesirable components into the plasma fraction.

In particular, hemolysis refers to the rupturing of erythrocytes (red blood cells) and the release of their contents, including hemoglobin and potassium, into surrounding fluid (e.g., blood plasma). Hemolysis may occur in vivo or in vitro (inside or outside the body). During any of the collection, transportation, and handling of patient whole blood samples, there is the possibility of hemolysis. If hemolysis occurs, the resulting components in the sample may cause interference in a number of tests, thereby leading to a signal reduction, reduced measurement accuracy and precision, or to false positive results at the other end of the spectrum. Further, if hemolysis occurs, it has been found that the potassium concentration in a corresponding sample may increase significantly and cause a high risk of misdiagnosis in a diagnostic test for potassium levels. See Clinical Chemistry, December 2003, vol. 49, no. 12, 2105-2106. Current methods do not adequately and quickly determine whether an unacceptable level of hemolysis has occurred in a blood sample.

BRIEF DESCRIPTION OF THE DRAWINGS

The invention is explained in the following description in view of the drawings that show.

DETAILED DESCRIPTION OF THE INVENTION

Aspects of the present invention are directed to devices, systems and methods that enable the quick and reliable detection of hemolysis in a sample such that a sample which exhibits an unacceptable level of hemolysis can be immediately flagged or disregarded in an associated diagnostic test. In this way, via the devices, systems, and methods described herein, a sample may be rapidly tested to determine whether hemolysis has occurred and a false positive result may be avoided, for example, a false positive result in an assay for potassium levels in a blood sample.

In one aspect, a device is provided to which a sample may be added and prepared for hemolysis analysis. In an embodiment, the device is removably insertable into a detection system such as a spectrometer to determine a degree of hemolysis. If a degree of hemolysis in the sample is above a predetermined threshold value, an indication of the same may be provided and proper action may be taken in response to an analytical test with the same sample or a second (other) sample from the same sample source. If the sample indicates that no hemolysis exists above a predetermined threshold level, further testing of the sample may be performed with greater confidence in the results, or the results of previously run diagnostic tests may be interpreted with greater confidence.

Figure 1:
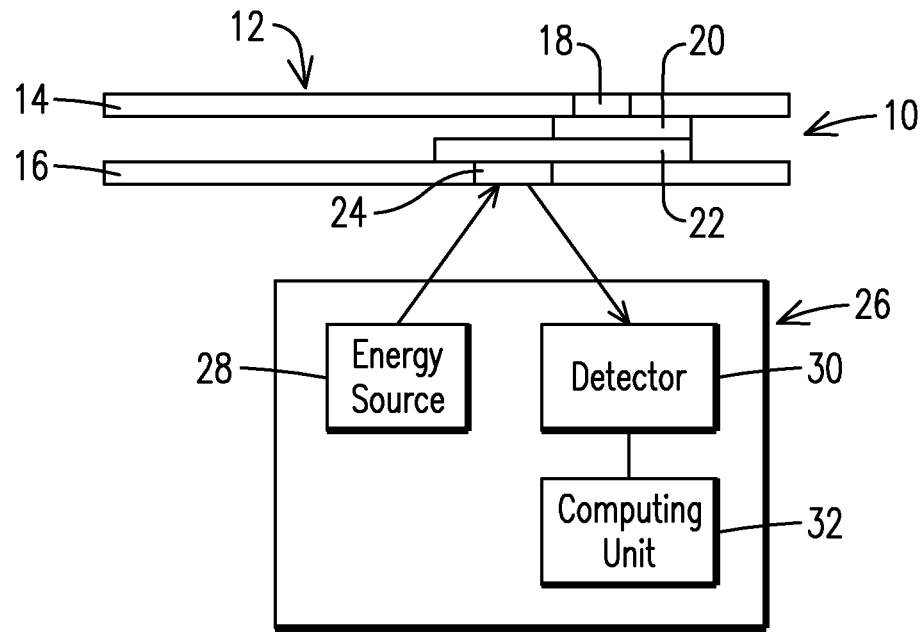
FIG. 1 illustrates a device for hemolysis detection in a sample in accordance with an aspect of the present invention.

Now referring to FIG. 1, there is shown an exemplary device 10 for hemolysis detection in a sample introduced into the device 10. In the embodiment shown, the device 10 comprises a body 12 having an upper portion 14 and a lower portion 16. In certain embodiments, the body 12 defines an opening 18 therein to allow for introduction of a sample into the device 10. The sample may be any sample suspected of having an unacceptable amount of hemolysis therein.

In the embodiment shown, the opening 18 is disposed in the upper portion 14 of the device 10, but it is understood the present invention is not so limited. Further, in the embodiment shown, a plasma separation element 20 is disposed within or carried by the body 12 of the device 10. The plasma separation element 20 is structured to isolate plasma and components from hemolysis (broken cell fragment, hemoglobin, etc.) from whole cells in a blood sample. A membrane 22 is disposed adjacent the plasma separation element 20 for receiving a plasma sample suspected of comprising an amount of hemolysis therein from the plasma separation element 20. A slit 24 may be defined in the body, such as in the lower portion 16, for defining a pathway for energy to be applied to the membrane 22 from an energy source 28 as will be discussed below in order to detect an amount of hemolysis in a sample.

The body 12 of the device 10 may be formed from any suitable liquid impermeable material that is also inert to at least hemoglobin. For example, without limitation, the body 12 may be formed from a material comprising polystyrene, polyethylene, polycarbonate, polypropylene, fluoropolymer, polyester, glass, metals, ceramics, suitable composite materials, and combinations thereof as would be appreciated by those skilled in art. As noted above, one or more openings 18 may be defined in the device for introduction of a sample to the device 10. The location, number, and size (e.g., width and depth) of the one or more openings 18 may be optimized for the desired application of the device 10.

The sample for introduction into the device 10 may be one that potentially has undergone an unacceptable amount of hemolysis therein. For example, the sample may be one which could potentially create a false positive result in an assay for potassium levels by providing potassium levels which are significantly larger than the associated subject's actual potassium levels in vivo in the absence of hemolysis. For example, potassium levels inside red blood cells may be 25 times higher than in plasma. Thus, if hemolysis occurs, the potassium value of the sample in question may be increased significantly. When a subject's potassium levels are not actually as high as indicated, a false positive result may in turn result in misdiagnosis and mistreatment of a disorder characterized by elevated potassium levels. For example, as a result of hemolysis, a subject might be misdiagnosed with having hyperkalemia or any other disorder or condition characterized by elevated potassium levels, e.g., Addison's disease or hemolytic anemia. Further, the subject may be misdiagnosed as having elevated potassium levels as a side effect of taking medications such as water pills (diuretics) or blood pressure drugs and unnecessarily instructed to cease taking such medications to the subject's detriment. In addition, a false positive result could inadvertently lead to one unnecessarily being provided with agents to remove potassium from the intestines before potassium is absorbed or other unnecessary treatments. Thus, advantageously, the device 10 may be utilized in a screening process for an unacceptable level of hemolysis prior to analysis of the sample for potassium levels or for confirming the integrity of test results already run.

In certain embodiments, the sample is a whole blood sample which includes a quantity of whole blood cells, including red blood cells, white cells, and platelets. Within the sample, the extent of hemolysis may correlate to an amount of hemoglobin therein. As used herein, it is understood that the term "hemoglobin" refers to any and all hemoglobin molecules obtained either from drawn blood or by recombinant procedures in their oxygenated, deoxygenated, dimeric, tetrameric, or various polymerized forms. Hemoglobin is commonly known as the oxygen-carrying pigment and predominant protein of red blood cells. Hemoglobin is composed of four protein chains, two alpha chains and two beta chains, each with a ring-like heme group containing an iron atom. Oxygen binds reversibly to these iron atoms. In its oxygenated state, hemoglobin may be referred to as oxyhemoglobin and is characterized by a bright red. In the reduced state, hemoglobin may be referred to as deoxyhemoglobin and is characterized by a purple-blue color.

In an embodiment, a presence of hemolysis in the sample is determined by analyzing at least for an amount of oxygenated hemoglobin in the sample. In a particular embodiment, the presence of hemolysis in a sample may be determined by a degree of discoloration of the sample or brought about by contact with the sample. As such, the more red the separated plasma sample, generally, the greater the amount of hemolysis that may have taken place.

It is appreciated that prior to analysis for an extent of hemolysis, it may be desirable to prepare the plasma sample by substantially filtering out whole blood cells from the sample, particularly in the case of a whole blood sample. It is further appreciated that this may be accomplished by a number of different methods, including but not limited to centrifugation, filtration, or the like. In an embodiment, a whole blood sample is separated to produce a plasma sample comprising hemolysed cells and the contents thereof (including hemoglobin) when hemolysis has occurred in the sample.

In an aspect of the present invention, a component for separating plasma and products of hemolysis (if present) is conveniently provided in the device 10. For example, in the embodiment shown in FIG. 1, the plasma separation element 20 is included which may isolate plasma and hemolysis products, e.g., hemoglobin, from whole blood cells in a sample such as a whole blood sample. In an embodiment, the plasma separation element 20 comprises a plasma separation membrane as is commercially available in the art. In certain embodiments, the plasma separation membrane comprises an asymmetric material, which is able to retain a plurality of whole blood cells thereon while allowing plasma and small molecules/complexes to travel therethrough. A number of different plasma separation membranes are commercially available and may be suitable for use in the device 10. For example, the plasma separation membrane may comprise an asymmetric polysulfone material as is commercially available from Pall Corporation (currently under the trademark Vivid™) Alternatively, the plasma separation element 20 may comprise any other suitable material or device that can provide a sample comprising plasma and components from hemolysis (if present) therein.

In operation, a sample 20 may be introduced onto the plasma separation element 20. After an effective amount of time, which may be two minutes or less, a retentate may be formed on the plasma separation element 20 which comprises whole blood cells, such as red blood cells, white blood cells, and platelets, while a filtrate passes through the plasma separation element 20 and onto the membrane 22. In other embodiments, a plasma portion may be formed by centrifugation or filtration remote from the device 10 and the resulting plasma portion may be introduced directly onto the membrane 22. In this instance, the device 10 need not include plasma separation element 20 and the device 10 may be further modified accordingly.

The membrane 22 may be any suitable porous or non-porous material which is inert to at least hemoglobin. For example, the membrane 22 may comprise a cellulosic material, a glass fiber material, a porous polymeric material, or combinations thereof. In one embodiment, the membrane 22 comprises a filter paper having a thickness sufficient to absorb and/or maintain a sample, such as the filtrate, thereon without adding any discoloration to the sample. For example, the membrane 22 may be any suitable commercial filter paper having sufficient degree of thickness to maintain the sample thereon such as a Whatman Grade 1: 11 µm pore size; 180 µm thickness; medium flow filter paper.

In certain embodiments, the body 12 of the device 10 comprises a slit 24 as referred to above. In an embodiment, the 24 is defined in the lower portion 16 of the device as shown in FIG. 1. The slit 24 defines a pathway for energy to be applied to the membrane 20 for the detection of hemolysis such as by spectroscopic methods. As such, the slit 24 (when present) will have a dimension, including a length and a width, suitable for a selected detection method as would be appreciated by one skilled in the art.

Figure 2:
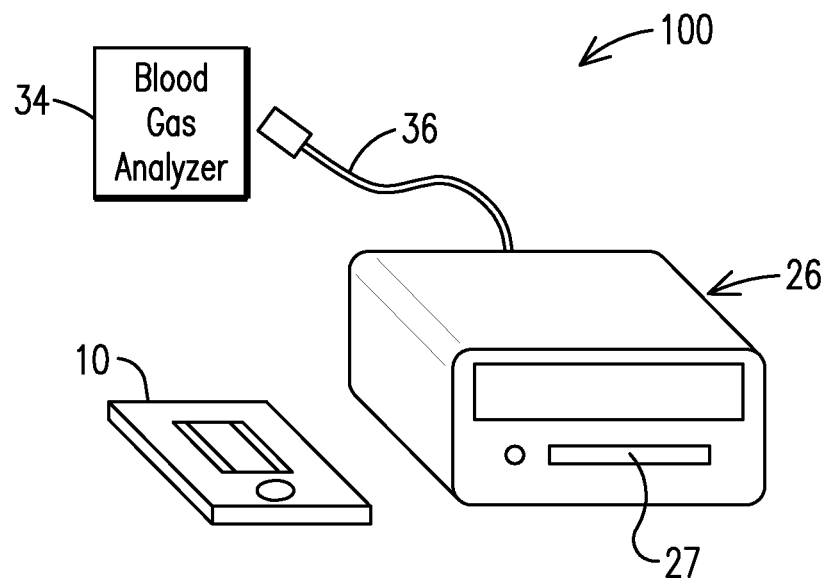
FIG. 2 illustrates a system for hemolysis detection in a sample in accordance with an aspect of the present invention.
Figure 3:
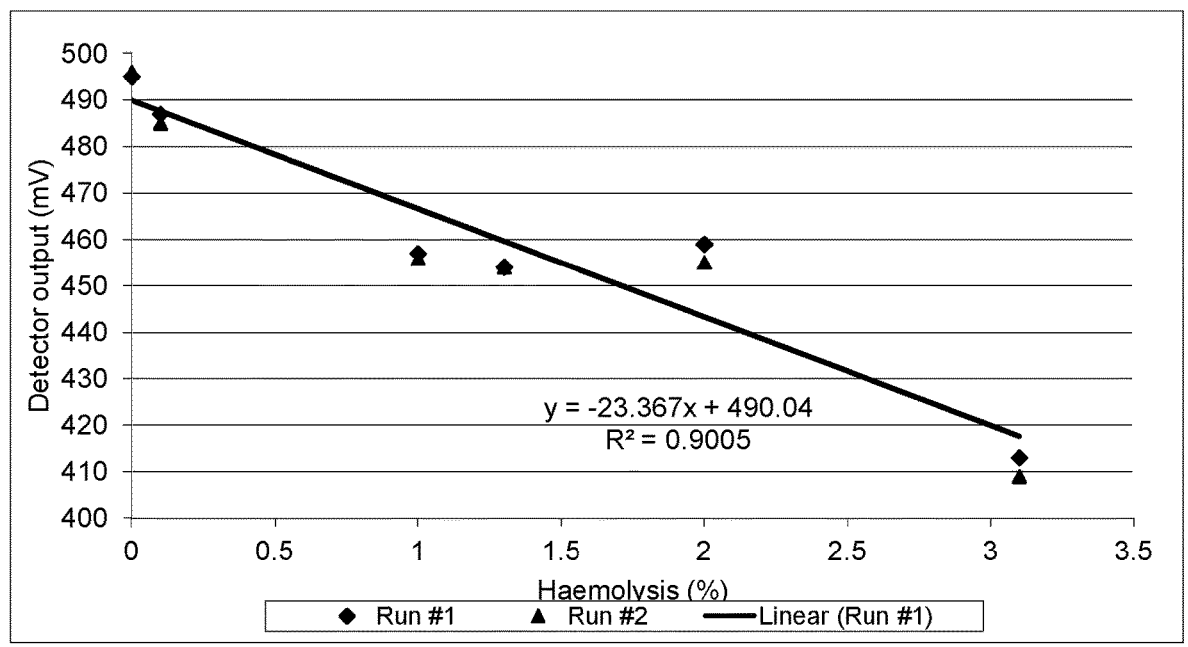
FIG. 3 is a graph showing a decrease in detector output signal as a function of increasing hemolyiss.

Referring now to FIGS. 1 and 2, the device 10 may be a component of a system 100 also comprising a detection system 26 for producing and recording an output indicative of the absence, presence, and, in certain embodiments, an extent of hemolysis in a sample introduced into the device 10. As such, the device 10 may be in a form suitable for removable insertion into or placement within the detection system 26 for analysis of the sample therein. For example, the device 10 may be in the form of a cartridge, cassette, or the like. Further, the device 10 may be formed from relatively inexpensive materials and may be readily disposable after a single use. In certain embodiments, the device 10 may be removably inserted into a corresponding receiving space 27 defined in a body of the detection system 26.

The detection system 26 may comprise any suitable apparatus for generating a qualitative, semi-quantitative, and/or quantitative result corresponding to an amount of hemolysis in the sample on the membrane 24. Thus, a detection system 26 that merely detects whether hemolysis in a sample is above a predetermined threshold is also considered to be included within the scope of the present disclosure. In a particular embodiment, the detection system 26 comprises a spectrometer as is well-known in the art comprising an energy source, a monochromator, the device 10 (when inserted), and a detector. The spectrometer is configured for scanning at least over a suitable range or at selected wavelength(s) for the detection of hemoglobin.

The amount of hemoglobin determined in a given sample is understood to be useful as a measurement of hemolysis. Thus, a threshold value for an acceptable amount of hemolysis will have an associated hemoglobin threshold value, which is readily determinable by one skilled in the art. If a sample has a hemoglobin content over the hemoglobin threshold value, it is understood that the sample may be said to have an unacceptable amount of hemolysis therein or also exhibits an amount of hemolysis over a hemolysis threshold value.

In an embodiment, as shown in FIGS. 1 and 2, the detection system 26 is configured to transmit energy from the energy source 28 to the membrane 22 through the slit 24 in the device 10 once the device 10 is inserted or otherwise properly associated with the detection system 10. Thereafter, a detector 30 is provided which is configured to receive and measure energy transmitted from the membrane 22 or energy absorbed by the membrane 22. The detector 30 may comprise a photomultiplier tube (PMT), a photodiode, or a charge coupled device (CCD) as are known in the art.

The generation of a spectrometric result on the system 26 may be carried out by known methods in the art such as those described in US Published Patent Application No. 20130084592, for example, the entirety of which is hereby incorporated by reference. In any case, the generated spectrum may be representative of the extent of hemolysis in the sample or on the membrane 22. In an embodiment, the extent of hemolysis may correspond empirically with a degree of coloration of the plasma fraction on the membrane 22. In a particular embodiment, an amount of oxidized hemoglobin in the sample corresponds with a degree of red coloration in the sample. The extent of hemolysis in a sample may thus be determined qualitatively, semi-quantitatively, or quantitatively through the use of known standards and controls as would be well understood by persons skilled in the art. For example, results may be compared to values of a calibration curve created from a plurality of standard samples having predetermined concentrations as is well-known in the art. In certain embodiments, any results on the system 26 may be compared to a predetermined threshold value to determine whether hemolysis in a subject sample is greater than an acceptable limit.

For system control and data management, the detection system 26 may comprise a computing unit 32 comprising one or more modules configured to receive data from the detector 30 and determine a degree of hemolysis from the data. The computing unit may comprise, for example, a special purpose computer comprising a microprocessor, a microcomputer, an industrial controller, a programmable logic controller, a discrete logic circuit or other suitable controlling device. In an embodiment, the computing unit 32 may further comprise one or more input channels, a memory, and output channel(s). The memory may include a computer-readable medium or a storage device, e.g., floppy disk, a compact disc read only memory (CD-ROM), or the like. In an embodiment, the computing unit 32 may comprise computer readable instructions for performing any aspect of the methods or for controlling any aspect of the components described herein.

In an embodiment, the computing unit 32 is programmed with instructions to provide an indication when determined that a degree of hemolysis in a subject sample is greater than a predetermined threshold value for hemolysis. In a particular embodiment, the predetermined threshold value is one over which would provide a potentially misleading result in a test for an analyte such as potassium. By "misleading," it is meant that the extent of hemolysis may be sufficient to alter interpretation of the result in a subsequent test for an analyte of interest. In such cases, an amount of hemolysis over the predetermined threshold may be sufficient cause a test to inaccurately reflect an amount of an analyte in question in vivo. The indication of hemolysis over a predetermined threshold may be conveyed to the test operator of the system 100 by any suitable method, such as an audio or visual alarm, or by providing the indication on a display or in a message, locally or remotely from the detection system 26. The predetermined threshold value may be, for example, an amount sufficient to provide a misleading potassium result in a subsequent test for potassium content within the same sample or a second sample which is/was taken from the same source. In a particular embodiment, the predetermined threshold value is one indicative of at least 0.5% hemolysis in a sample. In another embodiment, the predetermined threshold value represents at least 1.0% hemolysis. A 1% level of hemolysis, for example, may correspond to a 0.5 mmol/L increase in a potassium reading, which may lead to misdiagnosis or mistreatment.

In certain embodiments, the detection system 26 is configured for communication with an existing instrument which will test for potassium levels in a blood sample, such as a blood gas analyzer 34 (FIG. 2). Exemplary blood gas analyzers are available from Siemens Healthcare Diagnostics, Inc. and are currently sold under the trademarks: RAPIDLab 1200, RapidLab 348EX, RAPIDPoint 500, RAPIDLab 248/348, RAPIDPoint 400/405, RAPIDChem 744/754, and RAPIDPoint 340/350 Systems. In this way, the detection system 26 can act as a highly beneficial peripheral device to blood gas analyzer.

To accomplish this, the detection system 26 and blood gas analyzer 34 may comprise suitable wired or wireless connection(s) to facilitate communication therein such as a plug in connection as shown by exemplary USB connection 36. In an embodiment, a known sample from the same source (e.g., a sample taken from the same person at or about the same time) could be added to both the blood gas analyzer 34 and the detection system 26 comprising the device 10. By utilizing the detection system 26 as described herein, the detection system 26 may provide an indication that the sample introduced to the blood gas analyzer 34 is one that would likely or would be susceptible to providing misleading or less than optimal results by having a degree of hemolysis greater a predetermined threshold value. The indication may be an audio, visual, or written indication and may be output by any suitable method to any suitable location, component, report, or display. In this way, for example, samples which could potentially provide a misleading or false positive result for elevated potassium levels may be avoided or otherwise treated with appropriate caution.

Aspects of the present invention are demonstrated by the following examples, which are not intended to be limiting in any manner.

EXAMPLES

An experiment was carried out to confirm that hemolysis significantly decreases detector output (mV) as the degree of hemolysis increases. Whole blood samples with a range of 0 to 3.1% hemolysis were used and detection was measured at 540 nm. Tables 1 and 2 and FIG. 4, for example, shows a substantially linear decrease in detector output (mV) (measured at 540 nm) from 0 hemolysis to 3.1% hemolysis with a substantially notable plateau in the decrease of detector output from 1-2% hemolysis.

TABLE 1

Run #1

| Std (% Hemolysis) | Detector Output (mV) |
|---|---|
| 0 | 495 |
| 0.1 | 487 |
| 1 | 457 |
| 1.3 | 454 |
| 2 | 459 |
| 3.1 | 413 |

TABLE 2

Run #2

| Std (% Hemolysis) | Detector Output (mV) |
|---|---|
| 0 | 496 |
| 0.1 | 485 |
| 1 | 456 |
| 1.3 | 454 |
| 2 | 455 |
| 3.1 | 409 |

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A device for determining an amount of hemoglobin in a plasma fraction wherein the device comprises:
a body with an upper portion and lower portion formed from a liquid impermeable material that is also inert to at least hemoglobin;
an opening defined in the upper portion of the body for introduction of a blood sample;
a plasma separation membrane disposed between the upper portion and the lower portion, the plasma separation membrane positioned to receive the blood sample from the opening;
a second membrane having a first portion positioned adjacent to and below the plasma separation membrane so as to receive a plasma fraction from the plasma separation membrane that was separated from the blood sample by the plasma separation membrane; and
a slit defined in the lower portion of the body and defining a pathway for energy to be applied to the second membrane, the slit overlapping a lower surface of the second membrane in a second portion of the second membrane that is not underneath the plasma separation membrane.

2. The device of claim 1, wherein the plasma separation membrane comprises an asymmetric polysulfone material.

3. The device of claim 1, wherein the second membrane is constructed of a porous or non-porous material that is inert to at least hemoglobin.

4. The device of claim 1, wherein the second membrane is constructed of a cellulosic material, a glass fiber material, a porous polymeric material, or combinations thereof.

* * * * *